US008565865B2

(12) United States Patent
Belk et al.

(10) Patent No.: US 8,565,865 B2
(45) Date of Patent: Oct. 22, 2013

(54) METHODS FOR THE DETERMINATION OF T-SHOCK VULNERABLE WINDOW FROM FAR-FIELD ELECTROGRAMS IN IMPLANTABLE CARDIOVERTER DEFIBRILLATORS

(75) Inventors: Paul A. Belk, Maple Grove, MN (US); Jian Cao, Shoreview, MN (US); Jeffrey M. Gillberg, Coon Rapids, MN (US); Charles D. Swerdlow, Los Angeles, CA (US)

(73) Assignees: Medtronic, Inc., Minneapolis, MN (US); Imperception, Inc., Los Angeles, CA (US)

( * ) Notice: Subject to any disclaimer, the term of this patent is extended or adjusted under 35 U.S.C. 154(b) by 1371 days.

(21) Appl. No.: 12/178,850

(22) Filed: Jul. 24, 2008

(65) Prior Publication Data

US 2010/0023072 A1 Jan. 28, 2010

(51) Int. Cl.
*A61N 1/39* (2006.01)

(52) U.S. Cl.
USPC .......... 600/516; 600/508; 600/509; 600/510; 600/515; 600/517; 600/518; 607/4; 607/5; 607/9; 607/11; 607/18; 607/25; 607/26; 607/115; 607/116; 607/119; 607/122; 607/123

(58) Field of Classification Search
USPC ............ 607/4–5, 9, 11, 17–18, 25–25, 607/115–116, 119, 122, 123; 600/508–510, 600/515–518
See application file for complete search history.

(56) References Cited

U.S. PATENT DOCUMENTS

| 5,000,189 | A | * | 3/1991 | Throne et al. ............... 600/515 |
| 5,105,809 | A | | 4/1992 | Bach, Jr. et al. |
| 5,346,506 | A | | 9/1994 | Mower et al. |
| 5,564,422 | A | | 10/1996 | Chen et al. |
| 5,954,753 | A | | 9/1999 | Alt et al. |
| 6,477,422 | B1 | | 11/2002 | Splett |
| 6,675,042 | B2 | | 1/2004 | Swerdlow et al. |
| 7,181,275 | B2 | | 2/2007 | Havel |
| 7,181,285 | B2 | | 2/2007 | Lindh et al. |
| 7,257,441 | B2 | | 8/2007 | Swerdlow et al. |
| 2003/0195569 | A1 | | 10/2003 | Swerdlow et al. |
| 2004/0111120 | A1 | | 6/2004 | Sarkar et al. |

(Continued)

FOREIGN PATENT DOCUMENTS

| EP | 0536873 A1 | 4/1993 |
| EP | 0597431 A2 | 5/1994 |

(Continued)

OTHER PUBLICATIONS

PCT International Search Report; PCT/US2009/051376.

(Continued)

*Primary Examiner* — Christopher D Koharski
*Assistant Examiner* — Deborah Malamud
(74) *Attorney, Agent, or Firm* — Shumaker & Sieffert, P.A.

(57) ABSTRACT

Methods for determination of timing for electrical shocks to the heart to determine shock strength necessary to defibrillate a fibrillating heart. The timing corresponds the window of most vulnerability in the heart, which occurs during the T-wave of a heartbeat. Using a derivatized T-wave representation, the timing of most vulnerability is determined by a center of the area method, peak amplitude method, width method, or other similar methods. Devices are similarly disclosed embodying the methods of the present disclosure.

7 Claims, 8 Drawing Sheets

(56) References Cited

U.S. PATENT DOCUMENTS

| | | |
|---|---|---|
| 2004/0220631 A1 | 11/2004 | Burnes et al. |
| 2005/0038478 A1 | 2/2005 | Klepfer et al. |
| 2005/0065555 A1 | 3/2005 | Er |
| 2006/0235476 A1 | 10/2006 | Gunderson et al. |
| 2008/0033494 A1 | 2/2008 | Swerdlow |
| 2008/0269813 A1 | 10/2008 | Greenhut et al. |
| 2009/0093860 A1 | 4/2009 | Belk et al. |

FOREIGN PATENT DOCUMENTS

| | | |
|---|---|---|
| WO | 2004024231 A1 | 3/2004 |
| WO | 2004026398 A1 | 4/2004 |
| WO | 2004098704 A1 | 11/2004 |
| WO | 2006115940 A1 | 11/2006 |
| WO | 2009045610 A1 | 4/2009 |

OTHER PUBLICATIONS

Michael Shehata, M.D., et al., "Automatic Determination of Timing Intervals for Upper Limit of Vulnerability Using ICD Electrograms", PACE, vol. 31 691-700 (Jun. 2008).

Non-Final Office Action from U.S. Appl. No. 11/866,700 dated Mar. 14, 2011 (9 pages).

Response to Non-Final Office Action from U.S. Appl. No. 11/866,700, filed Jun. 14, 2011 (13 pages).

Amendment in response to Office Action dated Dec. 8, 2011 from related U.S. Appl. No. 12/178,903, filed on Mar. 8, 2012 having (11 pages).

Response to Rule 161(1) EPC communication from counterpart European Patent Application No. 09790716.6 dated Nov. 30, 2011 (8 pages).

Office Action from U.S. Appl. No. 12/178,903 dated Dec. 8, 22011 (19 pages).

Office Action from U.S. Appl. No. 12/178,903 dated Aug. 1, 2012 having (11 pages).

Amendment in response to final Office Action dated Aug. 1, 2012 from U.S. Appl. No. 12/178,903, filed Oct. 18, 2012 having (11 pages).

European Office Action from corresponding European Application No. 09 790 716.6-2305 dated Aug. 6, 2012 having (5 pages).

Response to European Office Action from corresponding European Application No. 09 790 716.6-2305 dated Feb. 18, 2013 having (9 pages).

\* cited by examiner

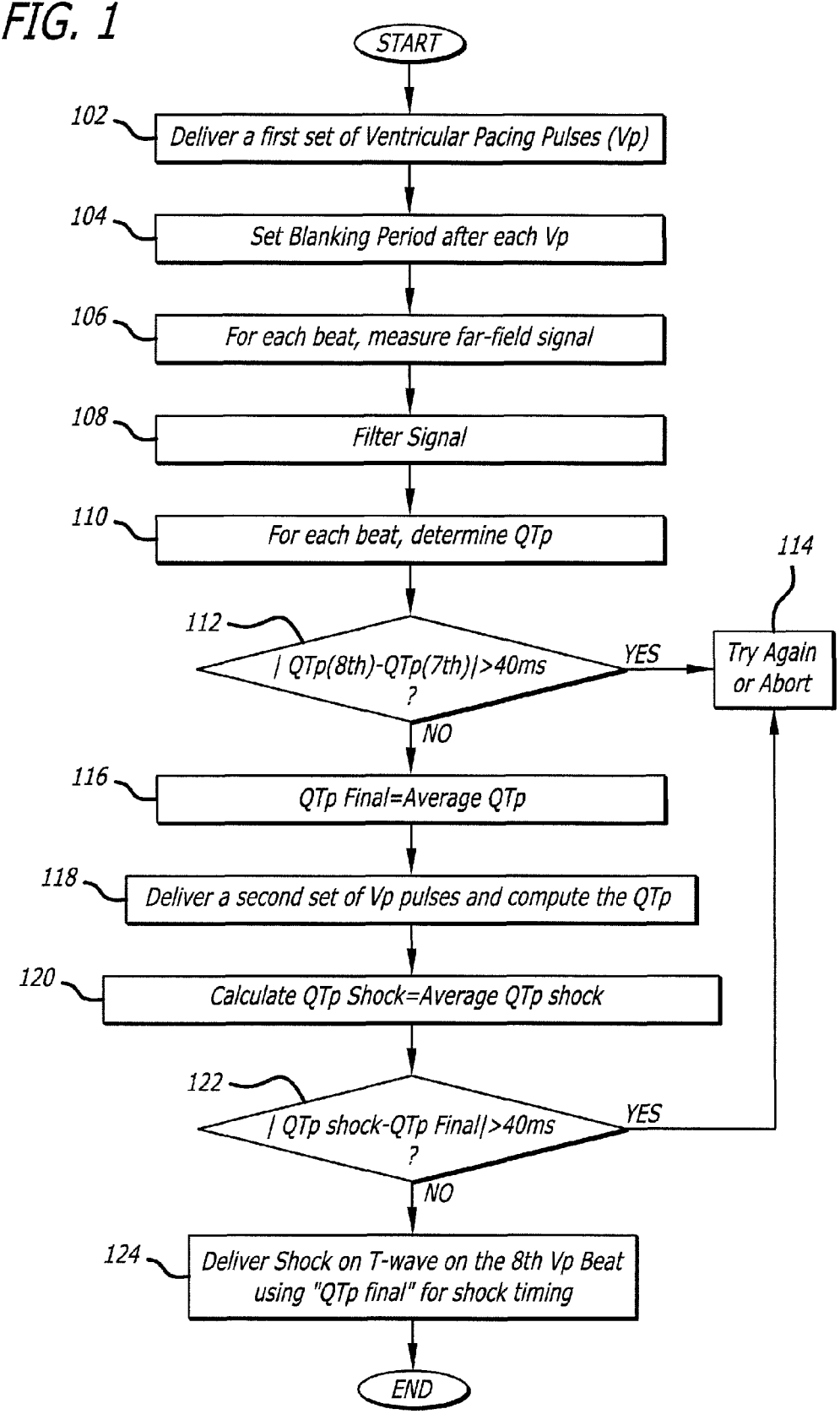

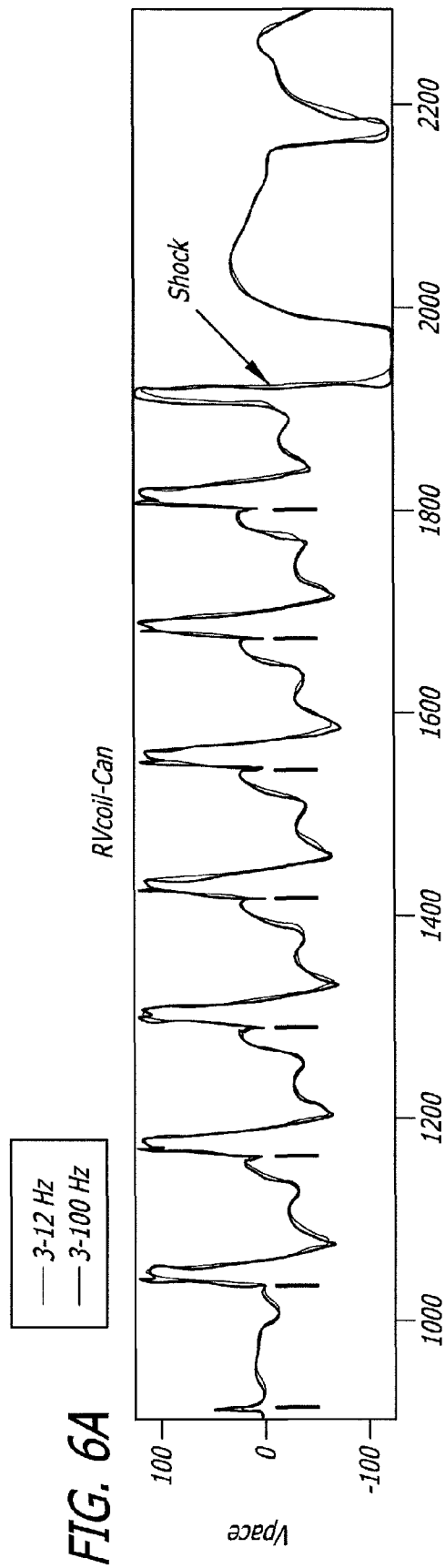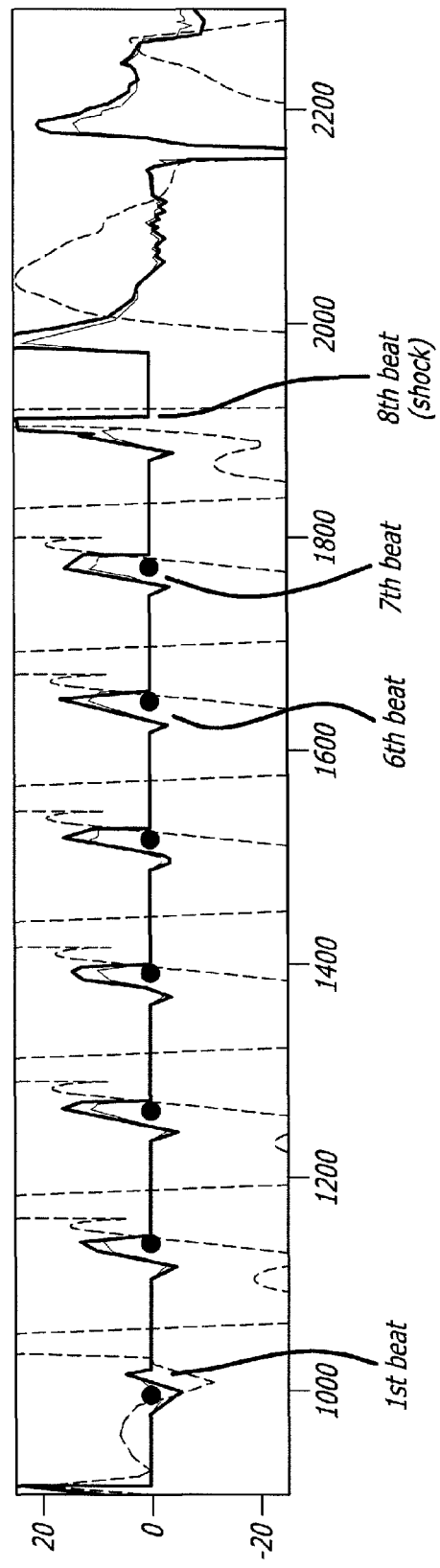
FIG. 6A
FIG. 6B

METHODS FOR THE DETERMINATION OF T-SHOCK VULNERABLE WINDOW FROM FAR-FIELD ELECTROGRAMS IN IMPLANTABLE CARDIOVERTER DEFIBRILLATORS

TECHNICAL FIELD

This disclosure relates generally to implantable medical devices (IMDs) and more particularly to methods for determination of shock timing for Upper Limit of Vulnerability (ULV) shocks.

BACKGROUND

A wide variety of IMDs have been developed in order to monitor patient conditions and deliver therapy to the patient. An IMD typically includes a hermetically sealed housing coupled to one or more leads that are surgically implanted inside a patient for sensing conditions or for administering therapy. The IMD may provide therapeutic stimulation to the patient or may deliver drugs or agents to the patient. Alternatively or additionally, the IMD may have sensing or monitoring capabilities. For example, the IMD may sense information within a patient and store the sensed information for subsequent analysis. In some cases, the sensed information may be used directly by the IMD to adjust or control the therapy that is delivered to the patent. It has been observed that the highest-energy shock that induces fibrillation in the heart of a patient, the Upper Limit of Vulnerability (ULV), is strongly correlated with the defibrillation threshold (DFT).

SUMMARY

It is therefore proposed to have the automatic methods for the timing of ULV shocks based on far-field electrograms (EGMs), which eliminates or reduces the need for a patient to undergo ventricular fibrillation (VF) induction to determine a shock strength sufficient to defibrillate a fibrillating heart.

In one or more embodiments, a method is provided for determining the timing for electrical shocks to be applied to the heart of a patient to determine the shock strength necessary to defibrillate a fibrillating heart. The timing corresponds the window of most vulnerability in the heart, which occurs during the T-wave of a heartbeat. Using a derivatized T-wave representation, the timing of most vulnerability is determined by at least one of a center of the area method, peak amplitude method, width method, or other similar methods. Devices are similarly disclosed for employing the methods of the present disclosure.

According to one or more embodiments, a method is disclosed comprising conditioning a heart with a plurality of ventricular pacing pulses, obtaining a far-field signal, calculating a value for the most vulnerable moment (QTp) for each heartbeat, and determining a time value in which the heart is vulnerable to electric shocks.

According to one or more embodiments, a method is disclosed comprising obtaining a derivatized EGM of far-field data for a set of heart heartbeats, determining a T-window for each heart heartbeat, and determining QTp for each heart heartbeat by calculating the center of the area of the derivatized EGM for the T-window.

According to one or more embodiments, a method is disclosed comprising providing a implantable medical device that at least is configured to provide ventricular pacing pulses and determines a period of vulnerability, wherein electrical shocks may be provided to defibrillate a fibrillating heart. The period of vulnerability is determined by obtaining a derivatized EGM of far-field data for a set of heart heartbeats, determining a T-window for each heart heartbeat, and determining a QTp for each heart heartbeat.

DRAWINGS

The above-mentioned features and objects of the present disclosure will become more apparent with reference to the following description taken in conjunction with the accompanying drawings wherein like reference numerals denote like elements and in which:

FIG. 1 is a flow diagram of an embodiment of a method of the present disclosure;

FIGS. 6A and 6B are graphical representations of an embodiment of the determination of QTp using the different methods of QTp determination disclosed herein;

DETAILED DESCRIPTION

Figure 2A:
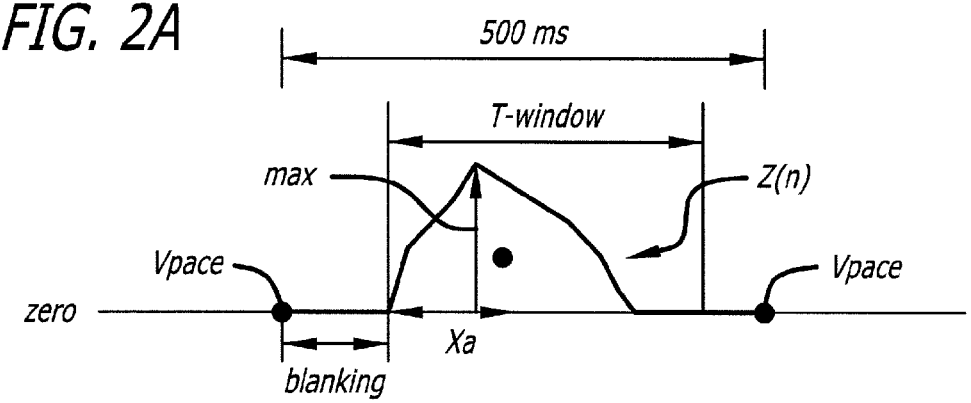
FIGS. 2A and 2B are a graphical representation of a T-window and flow diagram of an embodiment of a method for the determination of QTp.

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims. As used in the present disclosure, the term "or" shall be understood to be defined as a logical disjunction (inclusive of the term "and") and shall not indicate an exclusive disjunction unless expressly indicated as such or notated as "xor."

In one or more embodiments, novel methods and devices are provided for the determination of the timing of the most vulnerable window of the heart, which corresponds to the maximum positive slope in the T-wave of far-field electrograms (EGM). These methods may be embodied in implantable medical devices (IMDs) as described herein.

It is known that the maximum shock strength that will induce fibrillation of the heart is approximately the lowest shock strength necessary to defibrillate a fibrillating heart. Thus, a method of determining a sufficient shock strength to ensure a patient having an IMD is protected in case of fibrillation was discovered that does not require first inducing fibrillation. However, to successfully determine the appropriate shock strength, the most vulnerable window for the heart must be known.

According to embodiments, the methods of the present disclosure determine a most vulnerable window to be used in conjunction with the devices of the present disclosure. The methods are used to determine a shock strength that will reliably defibrillate a fibrillating heart without the need to induce fibrillation to determine an appropriate shock strength.

According to embodiments and as illustrated in FIG. 1, a method is shown for determination of a timing for delivering a shock that corresponds with the most vulnerable window for the heart. Generally, the method requires determining a heartbeat, such as by providing ventricular pacing pulses to condition the heart (i.e., put the heart into a known state) or by obtaining non-conditioned heartbeat data, followed by a measurement of a far-field signal. According to embodiments, the resulting signal may be filtered to remove unwanted noise and other artifacts not associated with the applicable heart measurements. Following the filtering, according to embodiments, a value for the most vulnerable moment (QTp) is calculated. Error checking steps may be used, according to embodiments, to ensure that the heart is behaving within a set of predetermined parameters allowing for useful determination of QTp.

According to embodiments, QTp may be used for ULV determination as set forth in the exemplary embodiments disclosed herein. QTp may also be used for other purposes as well, not merely for induction testing. For example and according to embodiments, the methods disclosed herein may be used to find the T-wave for patient monitoring or for facilitating therapies that are based on the current refractory period in the ventricle. Artisans will readily understand the modifications to the exemplary method disclosed herein would be necessary to accomplish other useful tasks using the data the methods of the present disclosure are used to generate.

More specifically and according to an exemplary embodiment where QTp is determined for the purpose of induction testing, FIG. 1 illustrates an embodiment of a method for determination of QTp. To make a determination of QTp, the heart may, according to embodiments, be conditioned to a known state in operation 102 whereby the time of the T-wave may be determined. According to other embodiments, T-peaks may be obtained from sinus or other intrinsic rhythms without preconditioning, for example, and the methods of the present disclosure adapted to determining timings based on the calculation of the T-peaks. Artisans will readily be able to adapt the principles disclosed in the methods herein to accomplish the same.

According to embodiments, because the T-wave window is the only relevant period of the heartbeat to the methods disclosed herein, a blanking period is determined and set that ignores the signal for the non-T-wave portions of the EGM in operation 104. The blanking window, according to embodiments, is set to guarantee that the T-wave is not part of the blanking window. According to embodiments, the blanking period represents an arbitrary time period, for example 280 ms, that is known to not contain the T-wave for a heart conditioned with ventricular pacing pulses. Thus, the T-wave as defined, according to the methods herein, may contain portions of the EGM that are not part of the T-wave, but which represent buffers on either side of the T-wave to ensure that no portion of the T-wave is included in the blanking period.

According to embodiments, determination of the blanking period in operation 104 may be juxtaposed with the measurement of the far-field signal in operation 106 or the measurement of the far-field signal and the filtering in operations 106 and 108. According to such embodiments, the EGM signal resulting from operation 106 is used to determine when the T-waves occur and the blanking period is set from the data collected. According to embodiments, an additional set of ventricular pacing pulses may be used for the purpose of determination of the blanking period when the data collected in the EGM are used to determine the blanking period; the additional set of pacing pulses are used set the blanking period, followed by the first set of ventricular pacing pulses that are delivered as illustrated in operation 102 used to determine QTp. According to embodiments, operation 104 may be omitted altogether by measuring the entire period between T-waves.

For each heartbeat or the total set of ventricular pacing pulses, a far-field signal is measured in operation 106. According to embodiments, any far-field signal or standard vector that substantially captures the electrical signal for a sufficient portion of the heart may used and implemented according to the methods and devices of the present disclosure. For example, one such vector or far-field signal may be RVcoil−(CAN+SVC) (right ventricle coil as the anode and the IMD Device+the superior vena cava coil as the cathode). Other examples for far-field signals exemplary of the far-field signals contemplated herein comprises RV-CAN, or RV-SVC, and other similar far-fields that capture substantially all of the electrical signal for the heart. Indeed, according to embodiments, electrodes of a typical electrocardiogram placed on the skin of a patient are used according to certain embodiments. Artisans will recognize far-field signals that substantially measure the electrical signal over substantially all the heart and can be used according to the methods and devices of the present disclosure.

According to embodiments, the only signal analyzed is that of the T-wave window. The T-wave window may be inferred from collected data as described above, according to embodiments, or arbitrarily set according to other embodiments. For example, the T-wave window may be set to 160 ms after the blanking period and EGM data collected only for the T-wave window.

According to embodiments, after the far-field EGM is obtained, the data is filtered to remove noise in operation 108. Many filters are applicable and will be known and understood to artisans without undue experimentation. According to embodiments, the filter step comprises two filters: a low pass filter and a differential filter. The low pass filter, according to embodiments, comprises a 12 Hz Butterworth filter for the EGM at 3-100 Hz (EGM Range =±8 mV, 8 bit 256 Hz in ICDs) according to the filtering formula:

$$y(n) = \frac{x(n+1) + x(n) + y(n-1) - \frac{y(n-1)}{4}}{8}$$

where x(n) is the input and y(n) is the output.

It was understood by a person of ordinary skill in the art at the time of the invention that a "Butterworth filter" uses a low pass filter design that implements adjusting the component values of the filter to compensate for the winding resistance of the inductors.

According to embodiments, the low pass filter is followed by a differential filter comprising a 5-point differential filtering of signal y(n) according to the following formula:

$$z(n) = -[2y(n-2) - y(n-1) + y(n+1) - 2y(n+2)]$$

where y(n) is the input and z(n) is the output.

According to embodiments, after the EGM is collected in operation 106 or the EGM is filtered in operation 108, QTp is determined for each heartbeat in operation 110. Determination of QTp may be accomplished according to numerous methods, as will be known and understood by artisans. Generally, the most vulnerable window for providing shocks to the heart occur where the slope of the T-wave is the greatest. Thus, using a derivatized representation of the T-wave, the most vulnerable moment will generally correspond with the x-axis value corresponding to the maximum derivatized value along the y-axis.

Figure 2B:
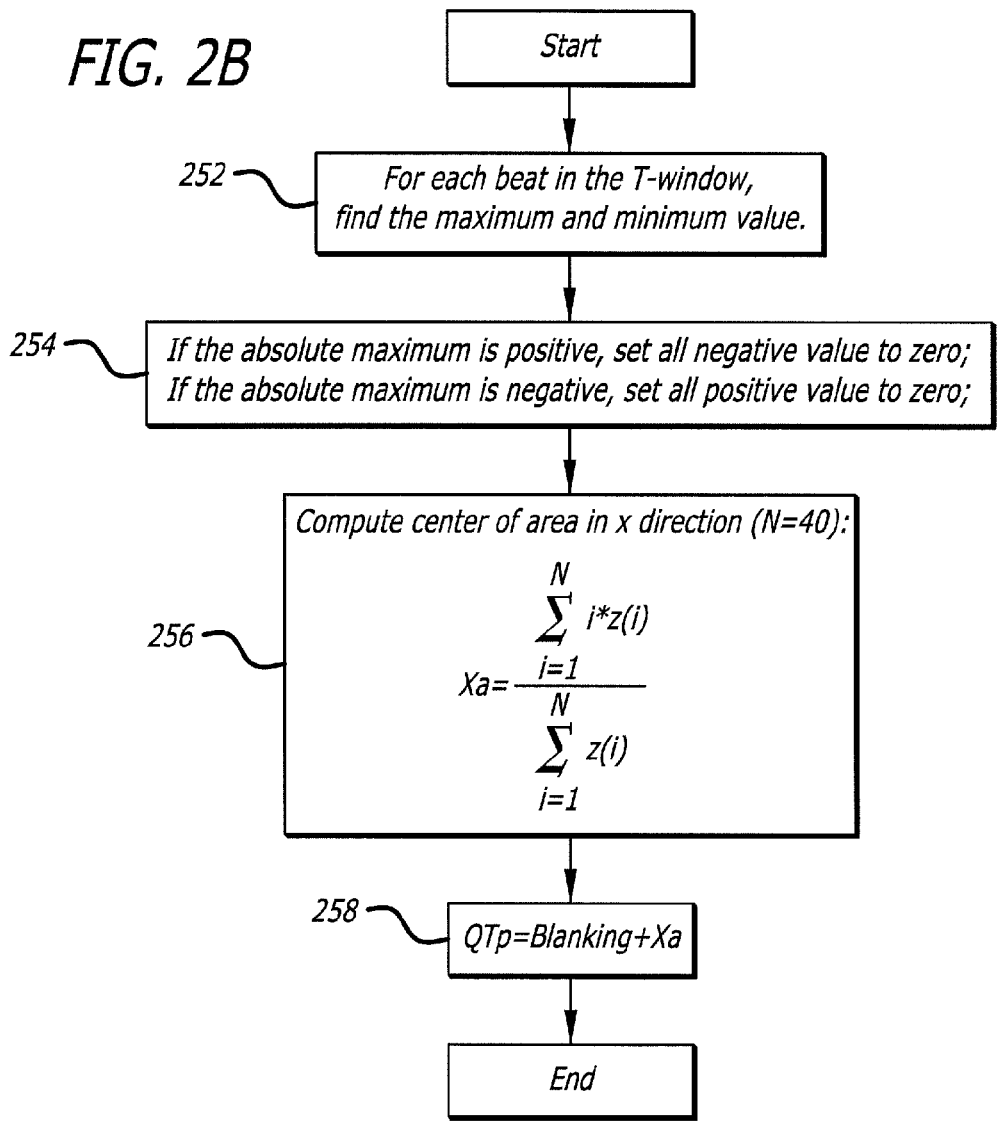

According to embodiments and as illustrated in FIG. 2, QTp is calculated by a center of area method. FIG. 2A illustrates an exemplary derivatized T-window. The center of area method assumes that the center of area is roughly equal to the point of the T-wave where the rate of change is greatest. The center of area method for determination of QTp is a method whereby the center of the area under the T-window is used to approximate QTp. As illustrated according to embodiments illustrated in the flow diagram of FIG. 2B, the center of area may be calculated by first determining the maximum and minimum values for each heartbeat in its respective T-window in operation 252. According to embodiments, it may be desirable to introduce a sign convention depending the polarity of the derivatized signal measurements. Thus, according to embodiments, if the absolute maximum is positive, all negative values are set to zero; if the absolute maximum value is negative, all the positive values are set to zero in operation 254.

According to embodiments, the center of the area for each T-window is computed in operation 256. According to embodiments, the center of the area for each T-window is computed according to the following equation:

$$Xa = \frac{\sum_{i=1}^{N} i * z(i)}{\sum_{i=1}^{N} z(i)}$$

for some arbitrary number of divisions of the T-window (N). According to embodiments, N=40, although other divisions are equally useful depending on the sensitivity desired, computing and electrical power available, and time limit desired to make computations, for example. Because Xa represents the time interval from the start of the T-window to the x-axis value corresponding to the center of area, QTp is calculated by adding Xa to the blanking period computed in operation 258.

Figure 3A:
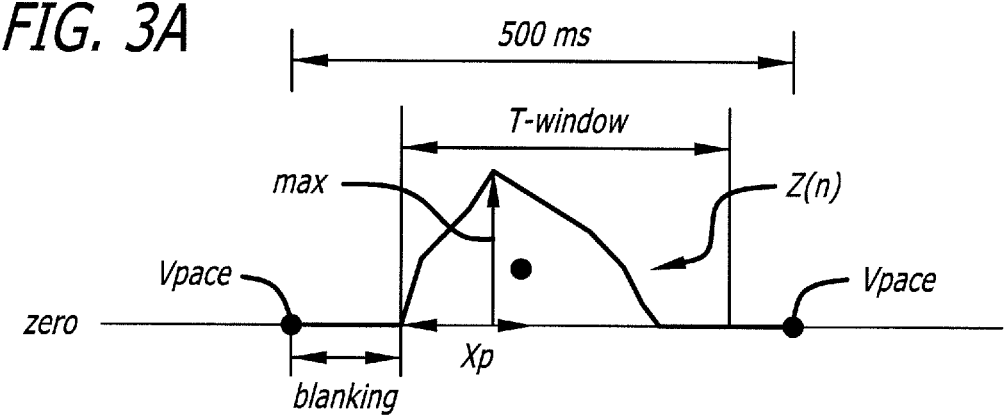
FIGS. 3A and 3B are a graphical representation of a T-window and flow diagram of an embodiment of a method for the determination of QTp.
Figure 3B:
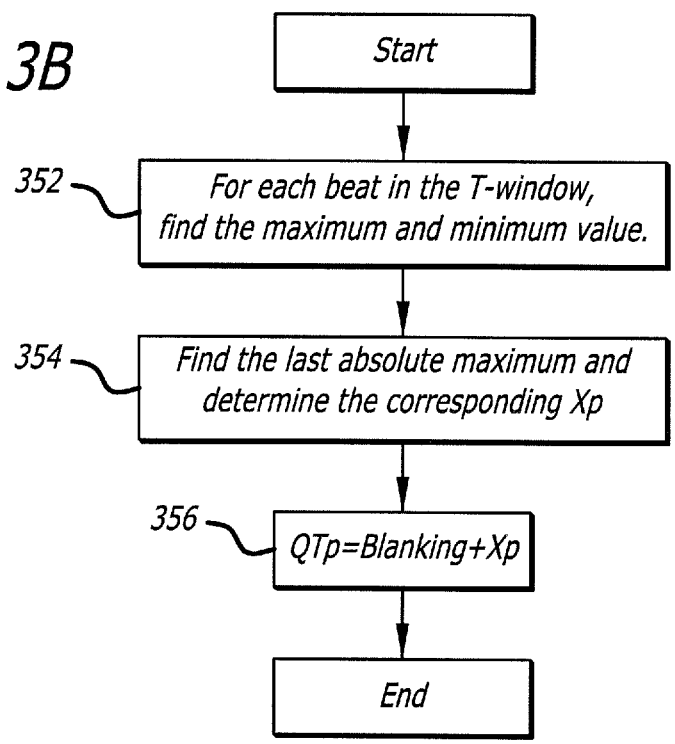

According to embodiments and as illustrated in FIG. 3, QTp is calculated by a peak amplitude method. According to the peak amplitude method, a derivatized T-window is used as in the center of area method. The peak area method assumes that the peaks represent the most vulnerable moments and calculates Xp (See FIG. 3A) be the x-axis value corresponding to the maximum EGM value along the y-axis during the T-window.

Accordingly, the peak amplitude method calculates QTp by searching for the peak amplitude of the derivatized T-wave, illustrated in FIG. 3A. According to embodiments and as illustrated in the flow diagram of FIG. 3B for each heartbeat in the T-window, the maximum and minimum values are determined in operation 352. The maximum value occurring with the highest value along the x-axis (i.e., the maximum occurring latest in time) becomes Xp in operation 354. QTp is determined by adding the blanking period to Xp in operation 356.

Figure 4A:
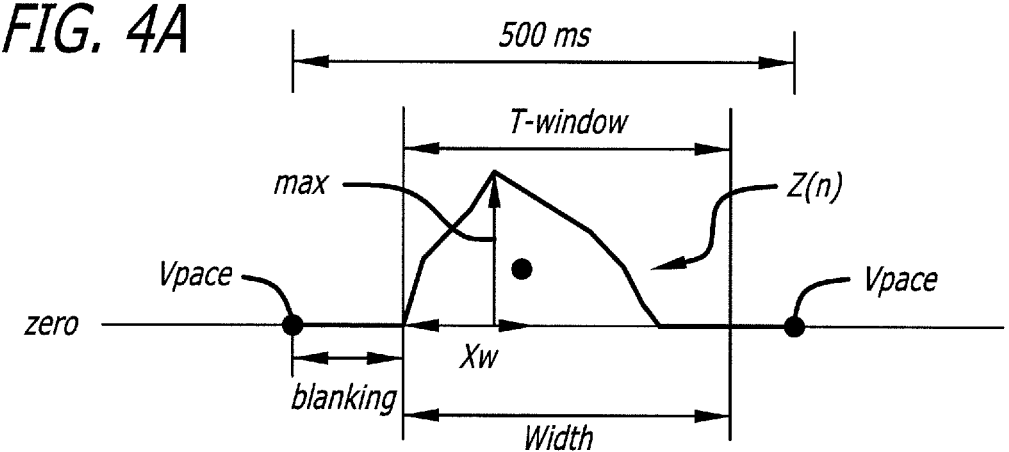
FIGS. 4A and 4B are a graphical representation of a T-window and flow diagram of an embodiment of a method for the determination of QTp.
Figure 4B:
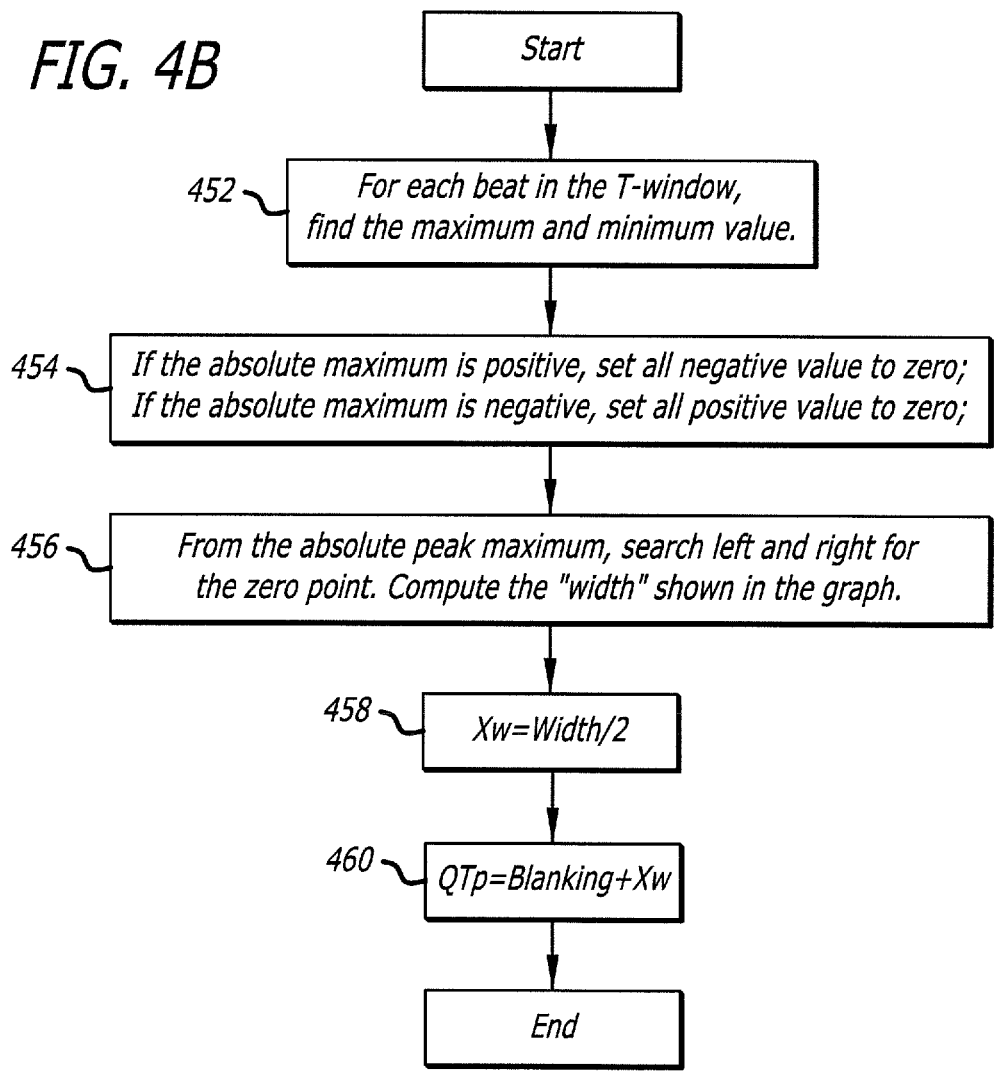

According to embodiments and as illustrated in FIG. 4, QTp is calculated by a width method. According to width method, a derivatized T-window is used. The width method assumes the greatest rate of change during the T-window occurs approximately half-way through the T-window (i.e., the T-window is assumed to be substantially symmetric).

Accordingly, the width method calculates QTp by finding the midpoint of the T-window and assume that point to be Xw (FIG. 4A). Like with the center of area method, the width method determines the minimum and maximum values for the T-wave in operation 452 and introducing a sign convention depending the polarity of the derivatized signal measurements in operation 454. Thus, according to embodiments, if the absolute maximum is positive, all negative values are set to zero; if the absolute maximum value is negative, all the positive values are set to zero in operation 454. The endpoints of the T-window are then computed from the absolute maximum value of the derivatized T-wave signal by looking along the x-axis for the closest zero values of the derivatized T-wave signal both ahead and behind the absolute maximum value in operation 456. The width of the T-window is the distance between each of these zero values along the x-axis. Xw is calculated as half of the calculated width in operation 458. In operation 460, QTp is computed by adding Xw to the blanking period.

Artisans will readily appreciate that other methods for calculating QTp are possible using the principles disclosed herein.

Referring again to FIG. 1, operation 112 represents an error checking step to ensure the values of QTp are within an arbitrary range of confidence. According to FIG. 1, if QTp measured in the $8^{th}$ heartbeat and QTp measured in the $7^{th}$ heartbeat differ by more than 40 ms, then the measurements are discarded and the process is restarted or aborted in operation 114. According to embodiments, a range of confidence may be used to determine whether the values of QTp vary enough to justify restarting the process or aborting the process. Similarly, any of the heartbeats may be substituted for the $7^{th}$ or the $8^{th}$ heartbeat values of QTp to perform the same function. Indeed, according to embodiments, aggregated functions may be used where the total difference of three or more QTp values cannot exceed a predetermined range of confidence. For example, the difference between the aggregated difference between the $6^{th}$, $7^{th}$, and $8^{th}$ heartbeats cannot differ by more than 70 ms.

If no error is detected in the error checking operations, then QTp Final is determined in operation 116. QTp Final represents a timing for the most vulnerable moment in which to provide a shock to the heart. QTp Final is calculated by calculating an average QTp. For example, QTp Final may be calculated by taking the sum of the final two QTp values and dividing by two. According to another example, QTp final may be calculated by taking the sum of all the QTp's for each heartbeat and dividing the sum by the total number of heartbeats in which QTp was calculated.

According to embodiments, the process of delivering ventricular pacing pulses and calculating a QTp for each heartbeat, as illustrated in operations 102 to 110 and described above, are repeated again in operation 118. During the second set of pacing pulses, the shock will be delivered according to QTp Final.

In operation 120, QTp Shock is calculated as an error checking process. QTp Shock is used to determine whether the shock pulse is going to be timed properly based on a comparison of the QTp's calculated in the set of first ventricular pacing pulses and in the second set of ventricular pacing pulses. QTp Shock is calculated as an average of QTp's for the second set of ventricular pacing pulses, as described above for QTp Final.

According to embodiments, the value for QTp Shock is subtracted from the value of QTp Final and the difference is taken in operation 122. If the resulting value is greater than some predetermined value, then the process is repeated or aborted in operation 114. According to embodiments, the predetermined value can be any useful value, for example 40 ms. According to embodiments, this error checking process is performed after the shock is delivered in operation 124, which creates an alert that the shock was potentially not delivered in the vulnerable window. According to other embodiments, the shock is not delivered unless the error checking in operation 122 passes.

Figure 5A:
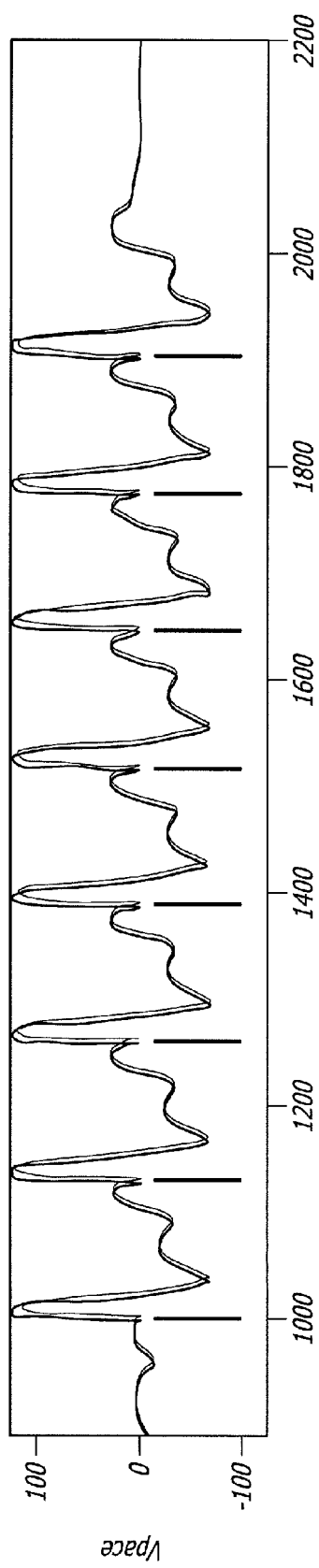
FIGS. 5A and 5B are graphical representations of an embodiment of the determination of QTp using the different methods of QTp determination disclosed herein.
Figure 5B:
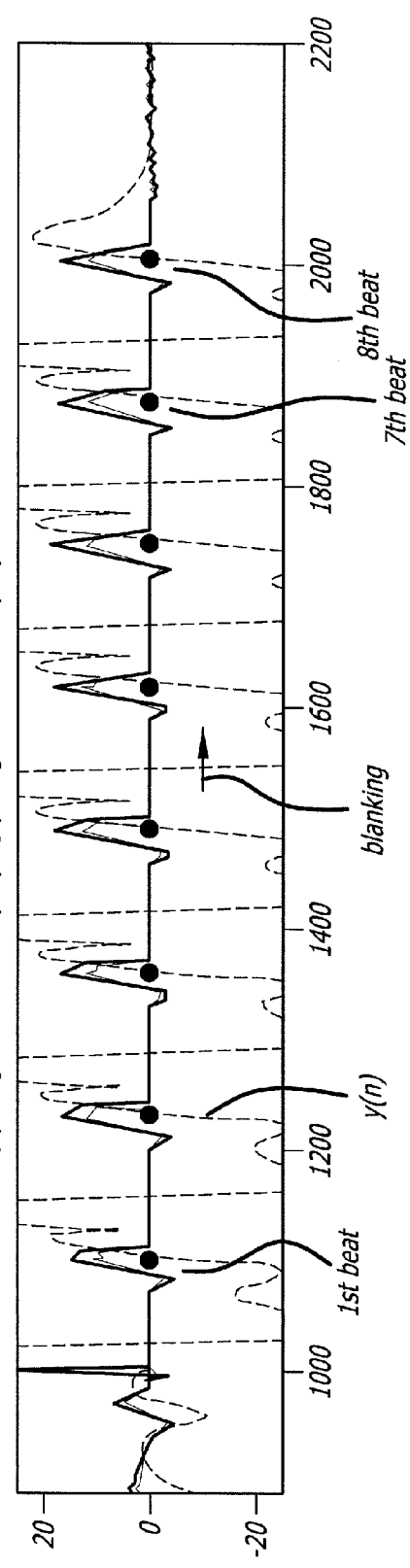

FIGS. 5A and 6A illustrate an exemplary far-field EGMs measuring RVcoil-CAN illustrating a first and second sets of ventricular pacing pulses respectively. Accordingly, FIGS. 5B and 6B illustrate derivatized values for the EGM. The horizontal stretching of FIGS. 5B and 6B illustrate the blanking periods. QTp's for the exemplary data were calculated using the center of area method (QTp1 alg1) and the peak amplitude method (QTp2 alg2). According to the exemplary set of data, both methods more or less closely approximated QTp for the exemplary data set.

According to embodiments, use of the QTp value allows for determination of a shock strength sufficient to defibrillate a heart without actually fibrillating the heart. The calculated QTp values determine the correct timing for delivery of such shocks, thereby providing the timing for which the shocks may be delivered.

According to embodiments, the methods disclosed herein may be implemented in devices, such as IMDs. IMDs may include sensing capabilities for monitoring physiological parameters or conditions and may include therapy delivery capabilities. IMDs may comprise any type of implanted device including, but not limited to cardiac pacemakers, implantable cardioverter-defibrillators (ICDs), implantable combination pacemaker-cardioverter-defibrillator (PCDs), or other types of implantable devices. Telemetry is used to communicate sensed information from the IMD to an external medical device for further analysis of the sensed information or to initiate further actions. Telemetry is further used to communicate information or instructions from external medical devices to the IMD.

Figure 7:
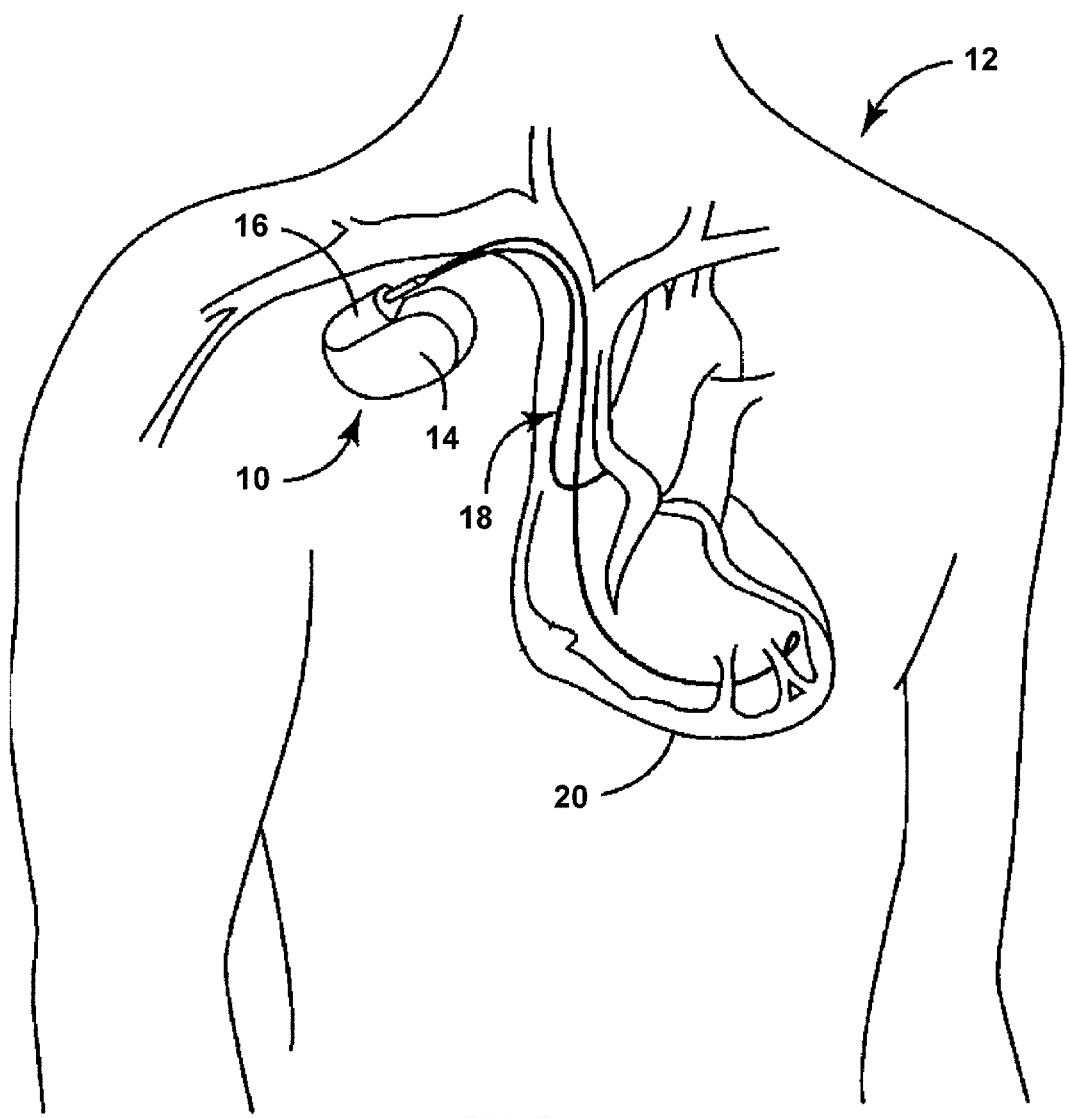
FIG. 7 illustrates an implantable medical device in accordance with an embodiment of the present disclosure implanted in a human body.

FIG. 7 is a simplified schematic view of one type of implantable medical device (IMD) 10 implanted within a human body 12 in which one or more embodiments of the invention may be implemented. IMD 10 comprises a hermetically sealed enclosure 14 and connector module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions. While IMD 10 is depicted in a pacemaker device configuration in FIG. 7, it is understood that IMD 10 may comprise any type of implanted device. IMD 10 collects and processes data from one or more sensors for deriving parameters used in computing a probability that an acute myocardial infarction (AMI) is occurring in the patient in which IMD 10 is implanted.

Figure 8:
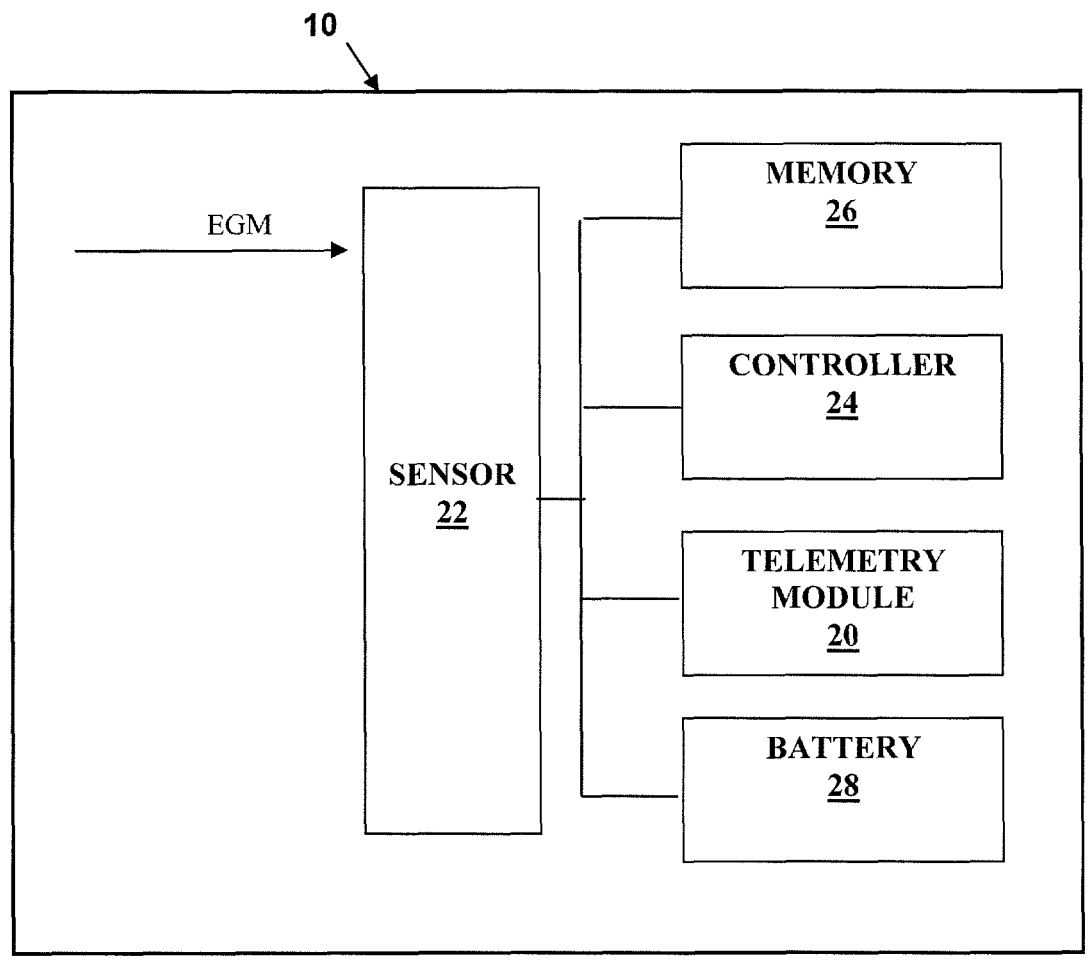
FIG. 8 is a block diagram illustrating the various components of an implantable medical device configured to operate in accordance with one or more embodiments of the present disclosure.

FIG. 8 is a block diagram illustrating the constituent components of IMD 10 in accordance with one or more embodiments having a microprocessor-based architecture. IMD 10 is shown as including telemetry module 20, at least one sensor 22, processor or controller 24, memory 26, battery 28 and other components as appropriate to produce the desired functionalities of the device.

Controller 24 may be implemented with any type of microprocessor, digital signal processor, application specific integrated circuit (ASIC), field programmable gate array (FPGA) or other integrated or discrete logic circuitry programmed or otherwise configured to provide functionality as described herein. Controller 24 executes instructions stored in memory 26 to provide functionality of the methods and devices as described herein. Instructions provided to controller 24 may be executed in any manner, using any data structures, architecture, programming language and/or other techniques. Memory 26 is any storage medium capable of maintaining digital data and instructions provided to controller 24 such as a static or dynamic random access memory (RAM), read-only memory (ROM), non-volatile random access memory (NVRAM), electrically erasable programmable read-only memory (EEPROM), flash memory, or any other electronic, magnetic, optical or other storage medium.

As further shown in FIG. 7, IMD 10 may receive one or more cardiac leads 18 for connection to circuitry enclosed within the housing 14. In one or more embodiments, IMD 10 collects electrocardiogram (ECG) signals or EGM signals for use in various methods described herein. Cardiac leads 18 may include, for example, pacing electrodes and defibrillation coil electrodes (not shown) in the event IMD 10 is configured to provide pacing, cardioversion and/or defibrillation. In addition, cardiac leads 18 may deliver pacing stimuli in a coordinated fashion to provide pacing pulses, cardiac resynchronization, extra systolic stimulation therapy or other benefits.

While the devices and methods have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising:
obtaining a derivatized electrogram (EGM) of far-field data for a set of heartbeats for a heart via an implantable medical device;
determining a T-window for each heart heartbeat via the implantable medical device; and
determining a most vulnerable moment (QTp) of the heart for each heartbeat via the implantable medical device by calculating the center of the area of the derivatized EGM for the T-window.

2. The method of claim 1, further comprising setting a sign convention.

3. The method of claim 1, wherein the center of area is computed using the equation $$Xa = \frac{\sum_{i=1}^{N} i * z(i)}{\sum_{i=1}^{N} z(i)}$$

where N is a predetermined value for the number of intervals to divide the T-window and z(i) represents a filtering of the far-field signal.

4. An implantable medical device configured to:
provide ventricular pacing pulses; and
determine a period of vulnerability for delivering electrical shocks to a heart via the implantable medical device;
wherein the implantable medical device is further configured to determine the period of vulnerability by:
    obtaining a derivatized electrogram (EGM) of far-field data for a set of heartbeats for the heart;
    determining a T-window for each heartbeat of the heart; and
    determining a most vulnerable moment (QTp) of the heart for each heartbeat by calculating the center of the area of the derivatized EGM for the T-window.

5. The implantable medical device of claim 4, wherein the implantable medical device is further configured to compute the center of area using the equation $$Xa = \frac{\sum_{i=1}^{N} i * z(i)}{\sum_{i=1}^{N} z(i)}$$

where N is a predetermined value for the number of intervals to divide the T-window.

6. The implantable medical device of claim 4, further configured for delivering shocks to the heart at times determined based on the determined QTp.

7. The implantable medical device of claim 6, wherein the implantable medical device is further configured to use the shocks to determine a shock strength that will defibrillate a fibrillating heart.

\* \* \* \* \*